(12) United States Patent
Mears

(10) Patent No.: US 6,436,108 B1
(45) Date of Patent: Aug. 20, 2002

(54) MOVABLE LIGATING BAND DISPENSER

(75) Inventor: Eric L. Mears, Duluth, GA (US)

(73) Assignee: EnSurg, Inc., Essex, MA (US)

( * ) Notice: Subject to any disclaimer, the term of this patent is extended or adjusted under 35 U.S.C. 154(b) by 0 days.

(21) Appl. No.: 09/552,670

(22) Filed: Apr. 19, 2000

(51) Int. Cl.$^7$ ............................................. A61B 17/10
(52) U.S. Cl. ...................................... 606/140; 606/139
(58) Field of Search .............................. 606/139, 140, 606/141, 148; 600/121, 114, 125

(56) References Cited

U.S. PATENT DOCUMENTS

| | | | |
|---|---|---|---|
| 3,760,810 A | 9/1973 | Van Hoorn | 128/326 |
| 3,911,923 A | 10/1975 | Yoon | 128/303 A |
| 4,226,239 A | 10/1980 | Polk et al. | 128/303 A |
| 4,257,419 A | 3/1981 | Göltner et al. | 128/303 A |
| 4,990,152 A | 2/1991 | Yoon | 606/140 |
| 5,207,690 A | 5/1993 | Rohrabacher et al. | 606/135 |
| 5,224,497 A | 7/1993 | Ehlers | 128/898 |
| 5,269,789 A | 12/1993 | Chin et al. | 606/140 |
| 5,308,353 A | 5/1994 | Beurrier | 606/144 |
| 5,320,630 A | 6/1994 | Ahmed | 606/140 |
| 5,337,734 A * | 8/1994 | Saab | 600/121 |
| 5,356,416 A | 10/1994 | Chu et al. | 606/140 |
| 5,398,844 A | 3/1995 | Zaslavsky et al. | 221/208 |
| 5,419,311 A * | 5/1995 | Yabe et al. | 600/121 |
| 5,462,559 A | 10/1995 | Ahmed | 606/140 |
| 5,507,797 A | 4/1996 | Suzuki et al. | 606/140 |
| 5,569,268 A | 10/1996 | Hosoda | 606/140 |
| 5,624,453 A | 4/1997 | Ahmed | 606/140 |
| 5,681,328 A | 10/1997 | Lamport et al. | 606/140 |
| 5,697,940 A | 12/1997 | Chu et al. | 606/140 |
| 5,735,861 A | 4/1998 | Peifer et al. | 606/139 |
| 5,788,715 A | 8/1998 | Watson, Jr. et al. | 606/140 |
| 5,814,062 A | 9/1998 | Sepetka et al. | 606/198 |
| 5,857,585 A | 1/1999 | Tolkoff et al. | 221/36 |
| 6,042,591 A | 3/2000 | Mears | 606/140 |
| 6,059,797 A | 5/2000 | Mears | 606/140 |
| 6,136,009 A | 10/2000 | Mears | 606/140 |

FOREIGN PATENT DOCUMENTS

| | | |
|---|---|---|
| EP | 0 310 582 A1 | 4/1989 |
| EP | 0 679 368 A1 | 11/1995 |
| WO | WO 95/12355 A1 | 5/1995 |
| WO | WO 96/19145 A1 | 6/1996 |
| WO | WO 96/24292 A1 | 8/1996 |
| WO | WO 97/45060 A1 | 12/1997 |

OTHER PUBLICATIONS

Directions for Use Brochure for Speedband™ Multiple Band Ligator, Microvasive Boston Scientific Corporation, pp. 1–8, 1995.

* cited by examiner

Primary Examiner—David O. Reip
Assistant Examiner—Julian W. Woo
(74) Attorney, Agent, or Firm—Sidley Austin Brown & Wood LLP (57) ABSTRACT

A ligating band dispenser capable of retraction during movement and exploration to offer an improved field of view for an image sensing device of a hosting endoscope as well as extension to facilitate a conventional ligating procedure.

24 Claims, 7 Drawing Sheets

MOVABLE LIGATING BAND DISPENSER

FIELD OF THE INVENTION

The present invention relates to a movable ligating band dispenser, and in particular, to a movable ligating band dispenser that can assume a retracted position, to provide a substantially unimpaired field of view for an image sensing device of a hosting endoscope or laparoscope as well as greater mobility during exploration for such devices, and an extended position, for enabling a conventional ligation procedure.

BACKGROUND OF THE INVENTION

Ligation is a medical procedure in which an elastic band, or ligating band, is placed about tissue to prevent fluid flow therethrough. Where a ligating band is placed about, for example, a ballooning varix, polyp, hemorrhoid, or precancerous lesion, a contracted ligating band induces fusion and healing in the base tissue and subjects the ligated tissue to necrosis. The necrotic tissue eventually separates from the surrounding tissue and passes into the human system. Alternatively, ligation may also be used for purposes of sterilization, wherein a ligating band may be placed over a folded loop portion of a Fallopian tube or a vas deferens to prevent the passage of internal reproductive fluids.

Means for delivering ligating bands, or ligating band dispensers, take various forms. One such form is a dedicated ligating band dispenser instrument which has a dispensing portion at a distal end, an actuating mechanism at a proximal end, and a typically rigid shaft therebetween. These instruments are useful for ligating tissue in which the user has access to the tissue to be ligated, e.g., tissue exposed through an invasive surgical procedure.

In contrast, ligating band dispensers may be positioned on the distal tip of an endoscope or a laparoscope. An endoscope is a conventional medical device used for viewing, exploring, and delivering therapies to internal regions of a patient. A laparoscope is a specialized endoscope for viewing a patient's peritoneal cavity. Unlike dedicated ligating band dispensing instruments, an endoscope allows minimally invasive intrusion into a patient.

Figure 1:
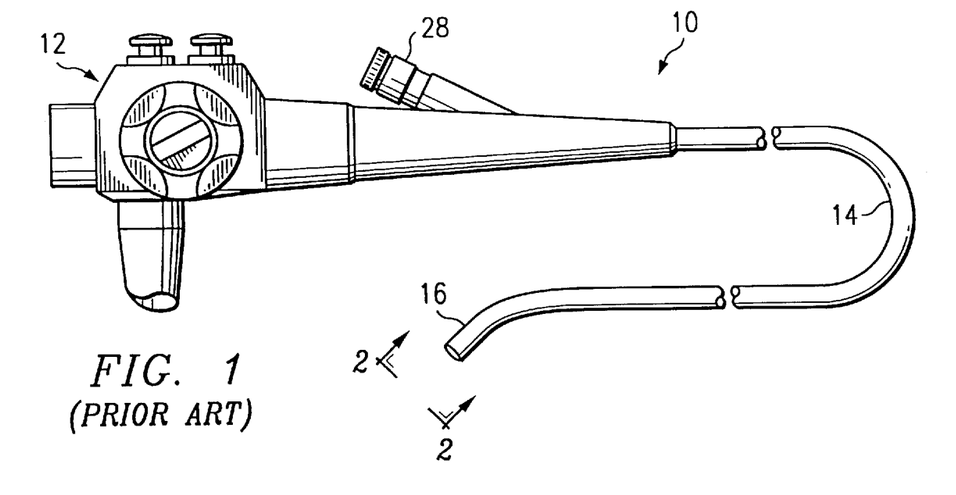
FIG. 1 illustrates a conventional endoscope.
Figure 2:
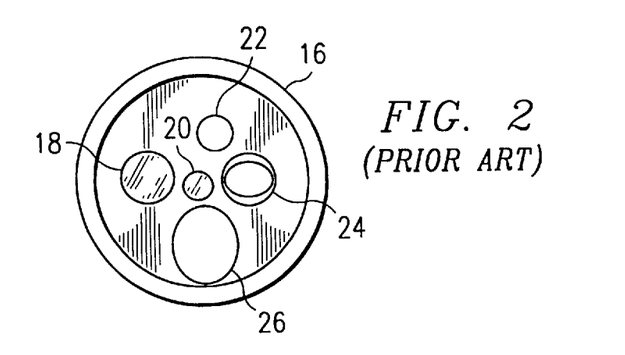
FIG. 2 is a view along line 2—2 of the insertion tip of the endoscope of FIG. 1.

FIGS. 1 and 2 illustrate a conventional endoscope. Endoscope 10 has a control portion 12 and a insertion portion 14 terminating at insertion tip 16. Insertion portion 14 is of such a length to permit access to internal regions of a patient.

FIG. 2 illustrates the face of insertion tip 16. A number of channels extend from the control portion 12 to the insertion tip 16, where the channels terminate in functional outlets 18–26. For the purposes of this example, outlet 18 is a light source; outlet 20 is a wide-field image sensing device, which transmits a video or fiber optic signal to a coupled monitor or eyepiece (not shown) at control portion 12; outlet 22 delivers a stream of water or air for clearing the image receiving device or flushing an internal bodily region; and outlet 24 is an outlet to a working (or biopsy) channel. Inlet 28 of the working channel can be coupled to a suction device or a lavage fluid source (not shown) or can receive various medical instrumentation (not shown) for passage through the working channel and outlet 24. Optional outlet 26, for larger diameter endoscopes, is an outlet for a second working channel. A second working channel allows additional operations in a manner consistent with the working channel described above.

Endoscope ligating band dispensers are fixedly mounted about and protrude from insertion tip 16 of a hosting endoscope, wherein such dispensers carry one or more expanded ligating bands about their outer diameter. Projecting from insertion tip 16, conventional dispensers inherently narrow the field of view of the image sensing device of outlet 20. In an effort to improve such impairment, some conventional devices are fabricated from a transparent material. While such material may facilitate the outward passage of light from outlet 18, such material does not practically improve the field of view for the wide-field image sensing device. Specifically, the use of transparent material commonly induces distortion about the periphery of a displayed image. Distortion is a product of both the curvature of the dispenser and the accumulation of bodily fluids about the outer surface of the dispenser. Ligating bands stored on the outer diameter of these dispensers further obstruct the field of view through the dispenser material.

Figure 3:
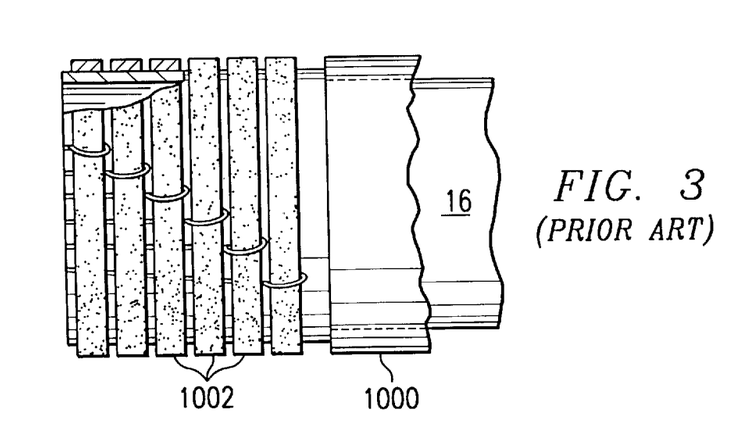
FIG. 3 illustrates a conventional ligating band dispenser.

A conventional endoscope ligating band dispenser is shown in FIG. 3. Dispenser 1000 is capable of dispensing multiple ligating bands 1002, whether individually or sequentially. Typical of the prior art, dispenser 1000 is cylindrical and hollow in nature, where an inner periphery of dispenser 1000 defines a cavity and an outer periphery carries the ligating bands 1002. Dispenser 1000 projects from the distal end of insertion tip 16. Accordingly, dispenser 1000 inhibits the field of view of a wide-field image sensing device (not shown) of the hosting endoscope in accordance with the limitations of conventional devices outlined above.

Conventional dispensers, such as dispenser 1000, increase the length of insertion tip 16. A ligating band dispenser-equipped endoscope is commonly used within a hollow body cavity, for example, an esophagus. Insertion tip 16 must assume almost a 90° bend with respect to the longitudinal axis of the insertion portion 14 to obtain a clear view normal to the inner surface of an esophagus. The additional length of the ligating band dispenser from insertion tip 16 can significantly restrict the motion and flexibility of insertion tip 16 within a hollow body cavity. Accordingly, the added length, coupled with the severely restricted peripheral view, makes the presence of conventional ligating band dispensers an operational liability during the exploration and placement phases of ligation procedures.

SUMMARY OF THE INVENTION

The present invention is directed to a ligating band dispensing device adapted to be movably received on a distal end of an insertion portion of an endoscope having a fixed seal. The dispensing device has a proximal end that movably receives an insertion portion of an endoscope, a distal end, and an interior surface that, when in an operative position, at least partially encompasses a portion of the insertion portion of the endoscope and at least a portion of the seal. The seal is adapted to establish a sealing relationship between the endoscope and the dispensing device during a ligation procedure. Operatively, the dispensing device is capable of movement from a retracted position to at least a dispensing position.

A dispensing device in accordance with another aspect of the present invention includes a ligating band dispenser, an actuating mechanism, and a sealing member for placement on the insertion portion of an endoscope. The ligating band dispenser is adapted to be slidably mounted on the distal end of the insertion portion of the endoscope. The actuating mechanism is coupled to the ligating band dispenser and is adapted to selectively effect movement of the dispenser from a first position to at least a second position, relative to the sealing member fixed to the insertion portion of the endoscope. In the second position, the distal end of the dispenser is distally spaced from the distal end of the endoscope, creating a volume substantially defined by the dispenser sufficient to perform a ligation procedure. In the first position, the volume is reduced to expose, at least in part, a face of the distal end of the insertion portion of the endoscope.

A system for dispensing a ligating band to ligate tissue in accordance with another aspect of the present invention includes an endoscope, a member, and a dispensing device. The endoscope has an insertion portion for insertion into a patient. The member is positioned on the insertion portion of the endoscope. The member further includes a proximal end that includes an abutting surface to abut a distal face of the insertion portion of the endoscope. The dispensing device is movably positioned on the insertion portion of the endoscope and is capable of movement from a retracted position to at least a dispensing position. At least a portion of the member is interposed between the dispensing device and the endoscope.

In operation, the present invention facilitates increased flexibility of motion and a greater field of view for an image sensing device of the hosting endoscope during a ligation procedure. More specifically, steps for ligating tissue may include providing a dispenser on a distal end of an insertion portion of an endoscope, said ligating band dispenser being coupled to a control portion with at least one control filament for selectively moving the dispenser from a retracted position to at least a dispensing position relative to the distal end of the insertion portion. The ligating band dispenser supports one or more expanded ligating bands. The insertion portion, including the dispenser is inserted into a patient, wherein the dispenser is in a retracted position relative to the distal end of the insertion portion. The insertion portion is then navigated to a desired tissue site. Once a tissue site is identified, the at least one control filament is manipulated so as to extend the dispenser to at least a dispensing position. The extended dispenser creates a volume substantially defined by the dispenser sufficient to receive that tissue to be ligated. Application of a suction or use of a mechanical instrument causes such tissue to be drawn into the volume, whereafter a ligating band can then be dispensed.

An object of the present invention is to provide an endoscope ligating band dispensing device which enables an improved field of view for an image sensing device of a hosting endoscope.

Another object of the present invention is to provide an endoscope ligating band dispensing device which may assume a first position for an increased field of view for an image sensing device of a hosting endoscope and may assume a second position for dispensing a ligating band.

Another object of the present invention is to provide a controller and an actuating device for an endoscope ligating band dispensing device to enable the selective retraction/extension of a ligating band dispenser as well as remote, selective ligating band dispensing.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 4A:
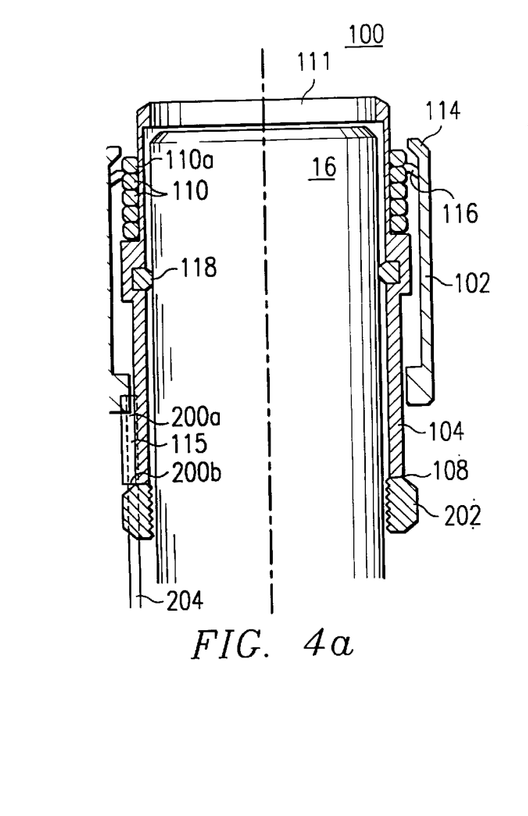
FIGS. 4a through 4c is a partial, sectional view of a movable ligating band dispenser of a first embodiment.
Figure 4B:
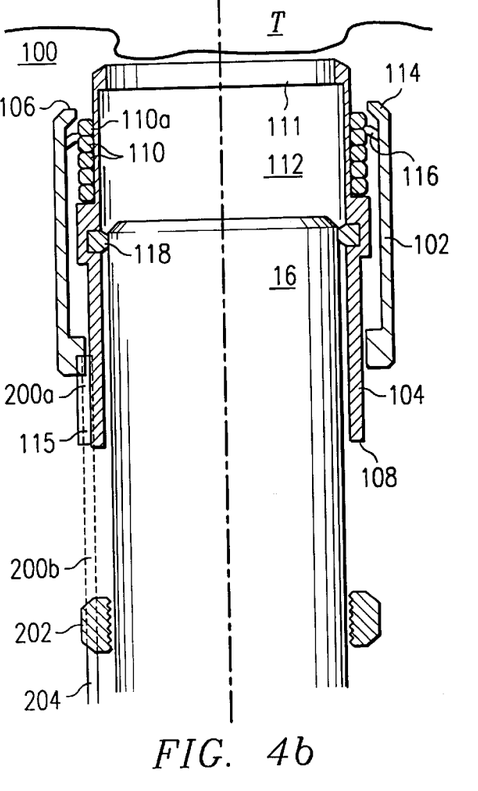
Figure 4C:
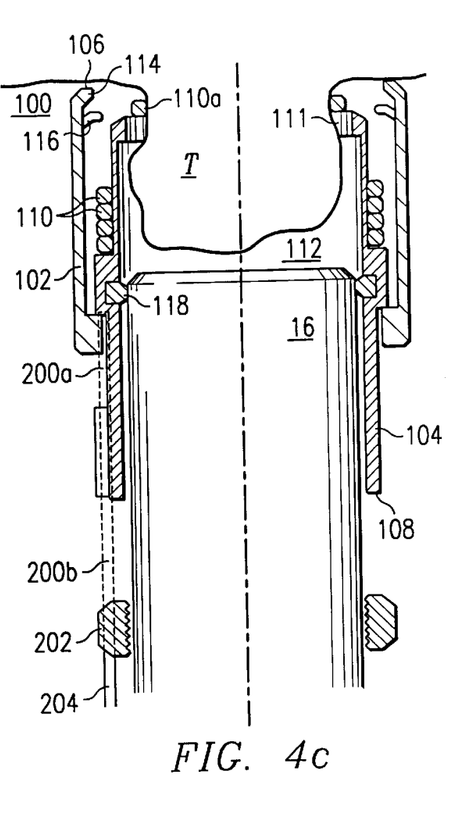

FIGS. 4a through 4c illustrate one embodiment of a movable dispenser 100. Dispenser 100 includes dispensing member (an outer sleeve) 102 slidably received on sleeve 104 (an inner sleeve), sleeve 104 being adapted to fit about insertion tip 16 of a hosting endoscope 10. Both dispensing member 102 and sleeve 104 have a cross-sectional shape consistent with the outer shape of insertion tip 16 of an endoscope 10, wherein such shape is typically circular in nature. Dispensing member 102 and sleeve 104 are constructed of a medical grade material suitable for exposure to a human system and which display low friction characteristics when in contact. Moreover, at least dispensing member 102 may be constructed of a transparent or translucent material to facilitate the passage of light when in an extended position (FIGS. 4b and 4c).

Referring to FIGS. 4a through 4c, dispenser 100 is generally cylindrical in shape and has a distal end 106 and a proximal end 108. The distal end of sleeve 104 defines opening 111 which has a diameter substantially consistent with the face diameter of insertion tip 16. Opening 111 allows use of the functional outlets 18–26 (FIG. 2) of the hosting endoscope, for example, transmission of light, passage of instrumentation, receipt of visual imaging, and the like. Sleeve 104 further includes a region, just proximal to its distal end, which carries at least one expanded ligating band 110. Preferably, however, sleeve 104 carries a plurality of expanded ligating bands 110.

Dispensing member 102 has a fixed shoulder 114 and one or more inwardly-biased, spring fingers 116. The distance between shoulder 114 and the aligned spring finger(s) 116 is approximately equal to the diameter (i.e., thickness) of a single ligating band 110. To limit undesired rotation of dispensing member 102, dispensing member 102 may include a recess or the like (not shown) along an inner surface to receive a longitudinal protrusion 115 which extends along an outer surface of sleeve 104. Alternatively, protrusion 115 could spiral about sleeve 104 (not shown), to induce a desired rotation, and facilitate a predetermined rate of extension of dispensing member 102 relative to sleeve 104.

Operation of dispenser 100 is illustrated by FIGS. 4a through 4c. FIG. 4a illustrates a first condition in which dispenser 100 is in a retracted position. Once tissue T for ligation is identified, dispenser 100 is extended to a dispensing position (FIG. 4b), thus creating volume 112, substantially defined by an inner surface of sleeve 104, to receive the chosen tissue T. To ready ligating band 110a, dispensing member 102 is drawn proximally until the spring fingers 116 are proximal to the distal-most ligating band 110a (FIG. 4b).

Volume 112 is subjected to a suction to draw tissue T therein (FIG. 4c), or tissue T is physically drawn into volume 112 using forceps (not shown) or the like which are passed through the work channel of endoscope 10 to the distal end 16 of dispenser 100. For dispensing, dispensing member 102, and thus ligating band 11a, are caused to move distally. When dispensing member 102 nears full extension, ligating band 110a is released. Following dispensing of the required number of ligating bands 110, dispenser 100 may again be retracted, and the sequence repeated, if desired.

In a retracted position, it is preferred that the distal end 106 of ligating band dispenser 100 be substantially aligned with the distal end of insertion tip 16. However, because certain ligating band dispensing mechanisms (i.e., those formed substantially along an inner periphery of dispenser 100 within chamber 112) may prevent this preferred position, a "retracted position" means a ligating band dispenser position which enables an improved field of view over a fully extended (or conventional) ligating band dispenser position and/or forms a volume, i.e., volume 112, insufficient to enable an effective ligation procedure.

As discussed above, a suction may be applied to draw tissue T into volume 112. Necessarily, a seal must be established between the insertion tip 16 of the endoscope 10 and sleeve 102 to efficiently maintain an applied suction. FIGS. 4a –4c show one embodiment of seal 118. More specifically, seal 118 is an o-ring type seal or v-ring, lip-type seal which slidably engages insertion tip 16 throughout the motion of sleeve 104. Seal 118 may also take the form of a rolling diaphragm 118' (FIG. 5) or an extension of sleeve 104.

Figure 5:
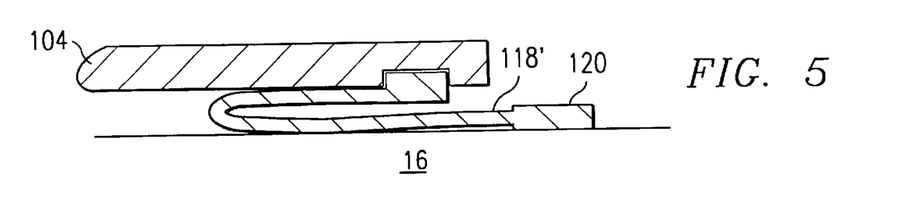
FIG. 5 is a partial, sectional view of a rolling diaphragm seal for an alternative embodiment of at least the movable ligating band dispenser of FIGS. 4a–4c.

For the first alternative, seal 118' includes a thin membrane coupled to dispensing member 102 and anchored to insertion tip 16. Seal 118' is joined to insertion tip 16 through application of an adhesive or, more preferably, by an integral elastic band 120 which tightly engages endoscope 10. As another alternative, a portion of sleeve 104 at or about proximal end 108 could be constructed of a flexible material which circumferentially extends about insertion tip 16. For this alternative, sleeve 104 can move relative to insertion tip 16 consistent with the above examples; however, when a suction is applied to volume 112 the flexible material is caused to contract about insertion tip 16 to both establish a seal and reduce those forces transmitted to actuating filament 200b due to the tendency of dispenser 100 to retract when the suction is applied.

While the above description sets forth three seal examples, one skilled in the art will appreciate that seal 118 (118') may take any variety of forms. At least for these embodiments, seal 118 (118') maintains a fluid-tight seal when dispenser 100 is at least in an extended position, and at least a portion of seal 118 (118') travels through the extension/retraction motion of dispenser 100.

Figure 9:
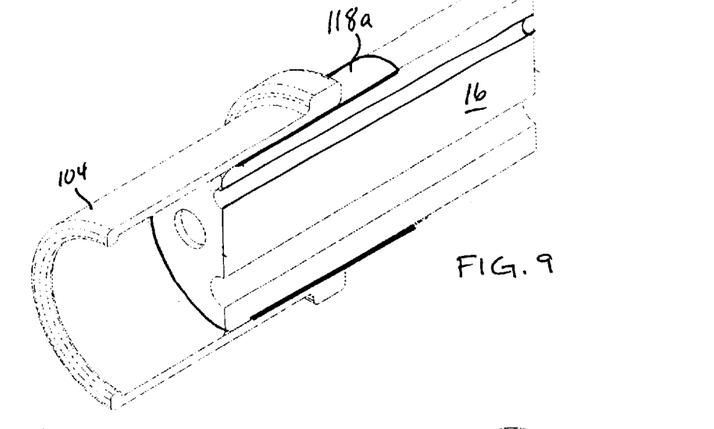
FIGS. 9–11 are partial, sectional perspective views of a movable ligating band dispenser operatively positioned relative to an insertion portion of an endoscope with alternative fixed seal structures.
Figure 10:
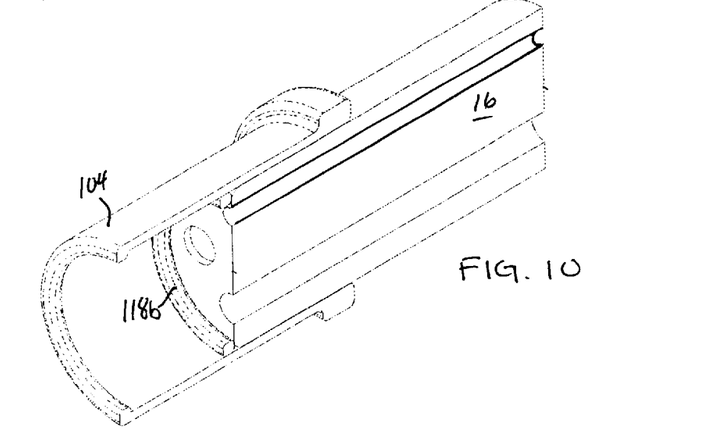
Figure 11:
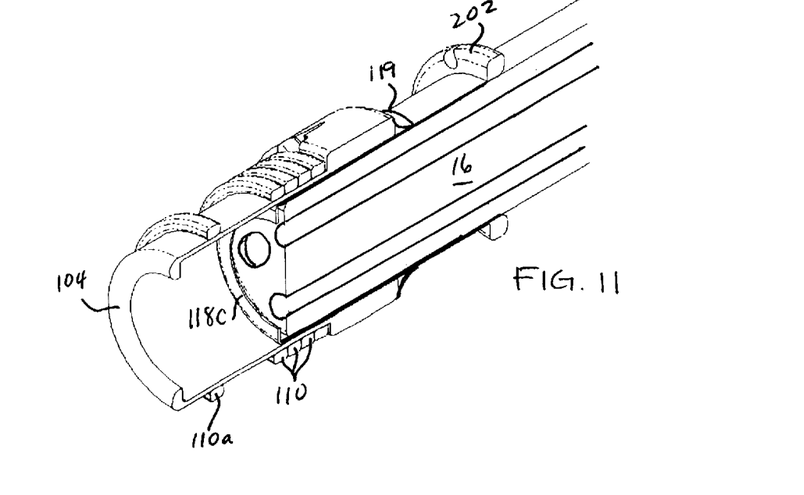

Additional seal configurations are illustrated in FIGS. 9–11. Generally, unlike seals 118 and 118' discussed above, structures 118a, 118b, and 118c are fixed relative to insertion tip 16 of a hosting endoscope 10 and function to establish a sealing relationship between insertion tip 16 and the movable sleeve 104. For FIGS. 9–11, the dispensing member 102 has been removed from the illustrations for clarity.

In reference to FIG. 9, seal 118a is a generally tubular structure, interpositioned between sleeve 104 and insertion tip 16, that operatively establishes a seal between insertion tip 16 and sleeve 104 throughout at least a portion of the range of motion of sleeve 104. In a preferred configuration, however, a seal is established through a whole range of motion of sleeve 104. Seal 118a (as well as seals 118b and 118c) can be formed of effectively any rigid or elastomer medical grade material capable of establishing a seal at an interface of two such materials. To this end, while seal 118a could be formed of a rigid material (e.g., stainless steel, thermoplastics, etc.), it is preferable that seal 118a be formed of a medical grade elastomer material.

As one variation, seal 118a, having a largely uniform material thickness, extends between sleeve 104 and insertion tip 16 for a length of seal 118a. Alternatively, seal 118a may have an uneven thickness, which gradually increases, for example, from a proximal end to a distal end of seal 118a. With this thickness variation, seal 118a can maintain a maximized length to assist in holding its position relative to insertion tip 16 during operation but also minimize the surface area in friction contact with sleeve 104. As well, for seal 118a, either an inner surface or an outer surface, or both, may include ridges, ribs, or the like to facilitate the sealing relationship between insertion tip 16 and the movable sleeve 104.

In another form, seal 118a does not frictionally engage sleeve 104. Rather, a small clearance is provided therebetween to enable free movement of sleeve 104 relative to insertion tip 16. Depending on the magnitude of such clearance, flap 119 (FIG. 11) can be provided on a proximal end of sleeve 104. In operation, when a vacuum is applied to volume 112, flap 119 deforms inwardly to establish a proper seal with the proximal portion of seal 118a. However, when such clearance is slight, which is more typical, application of a vacuum to volume 112 will effect a sealing relationship between sleeve 104 and seal 118a and the additional structure of flap 119 becomes unnecessary.

FIG. 10 illustrates a perimeter seal (e.g., an o-ring), seal 118b, that is fixed proximate to the face of insertion tip 16 to frictionally engage an interior surface of dispensing member 102 throughout a range of motion of dispensing member 102. Seal 118b is preferably formed of a medical grade elastomer material.

Seal 118b can be constructed as a permanent part of insertion tip 16 or added, using an adhesive or the like, to insertion tip 16 at the time of a procedure. As another alternative, seal 118b could include a proximal sleeve portion, structurally similar to that of seal 118a, which would allow seal 118b to be positioned relative to the face of insertion tip 16 quickly and easily, with or without the need for adhesive. Specifically, a practitioner would pass insertion tip 16 of a hosting endoscope 10 through the sleeve portion, which would be diametrically sized to tightly grip insertion tip 16, until seal 118b is positioned proximate to the face of insertion tip 16. Referring to FIG. 11, seal 118c, or more appropriately structure 118c, has a cylindrical form that fits about insertion tip 16. At a distal end, a sealing structure similar to seal 118b (not shown) can be provided.

If such a sealing structure is present, a sealing relationship is operatively established between insertion tip 16 and sleeve 104 in a manner consistent with seal 118b described above.

As an alternative, structure 118c can be formed with an inwardly directed portion, as shown in FIG. 11. This portion, if provided, assists in the placement and retention of structure 118c and dispenser 100 relative to insertion tip 16. For at least this variation, structure 118c is preferably constructed of a substantially rigid material, wherein the inwardly directed portion of structure 118c resists a proximal movement of structure 118c through the inwardly direction portion's contact with the face of insertion tip 16. Undesirable proximal movement of structure 118c/dispenser 100 could otherwise occur during movement of insertion tip 16 through a patient, during actuation of dispenser 100 to a dispensing position (described in greater detail below), or the like.

At a proximal end, seal 118c can includes an integral structure that can serve as a proximal seal and/or function in a manner equivalent to ring 202 (i.e., to serve as a point of engagement for an actuating mechanism). Intermediate to its proximal and distal ends, seal 118c has a generally tubular form consistent with that discussed above in regard to seal 118a. Accordingly, whether seal 118c is formed of a rigid material or an elastomer-type material, this intermediate position is capable of establishing a sealing relationship in a manner consistent with seal 118a.

While FIG. 11 shows sleeve 104 having flaps 119, such arrangement is for illustrative purposes only. In the event that sleeve 104 and seal 118c are in friction contact or a clearance between sleeve 104 and seal 118c is such that additional sealing components are not required, the provision of flaps 119 is not necessary to establish a proper seal between these structures.

Dispenser 100 is extended and retracted using an actuating mechanism. An actuating mechanism in accordance with the present invention includes actuating elements 200, which are coupled between dispenser 100 and controller 150, which will be discussed in greater detail below.

FIGS. 4a–4c illustrate one embodiment of actuating elements 200. Actuating elements 200 are preferably semi-rigid filaments or thin cable (collectively "filaments") formed from PVC, nylon, Kevlar® (E.I. du Pont de Nemours and Company, Wilmington, Del.), stainless steel, nitinol, or the like. For this embodiment, actuating filaments 200 are exterior to and extend along the outer surface of insertion portion 14. Actuating filament 200a is coupled to dispensing member 102 and effects movement of the dispensing member 102, while actuating filament 200b is coupled to sleeve 104 to effect retraction/extension of dispenser 100. In operation, distally-directed forces applied to filaments 200a, 200b cause an extension of dispensing member 102 and sleeve 104, respectively, while a proximally-directed force applied to filaments 200a, 200b cause a retraction of the same. In some instances, certain actuating elements 200 can perform multiple tasks to simplify operations, for example, a distally-directed force applied to actuating filament 200b can effect the extension of both members 102, 104 and, when dispenser 100 is extended, a proximally-directed force applied to actuating filament 200b can effect a retraction of both members 102, 104. While these embodiments of actuating element 200 operate in response to the application of axial forces, actuating elements 200 could include features to effect extension/retraction of dispenser 100 and/or dispensing of ligating bands 110 in response to an applied rotation.

Actuating filaments 200a, 200b pass through grasping ring 202. Preferably, ring 202 is an independent elastic band which is positioned proximal of dispenser 100 and tightly holds to the insertion tip 16. Preferably, filaments 200a, 200b are covered with a load bearing encasement 204, which terminates at and is integral with ring 202. Operatively, ring 202 asserts a force against casing 204 which is at least equal and opposing to any distally-directed forces applied to actuating filaments 200a, 200b. Ring 202 may further include securing means to receive and releasably secure sleeve 104 in a retracted position. If not independent, ring 202 can dually serve as the anchor 120 for the rolling diaphragm seal 118' of FIG. 5. For this embodiment, actuating filaments 200a, 200b may be further secured along the length of the insertion portion 14 with tape, adhesive, additional elastic bands, a spiral wrap of actuating filaments 200a, 200b about insertion portion 14, or the like.

FIGS. 6a–6d illustrate other embodiments and combinations of actuating elements 200. Common to these embodiments, however, actuating elements 200 pass through outlet 24 and extend internally through the work channel of insertion portion 14 to inlet 28.

Figure 6A:
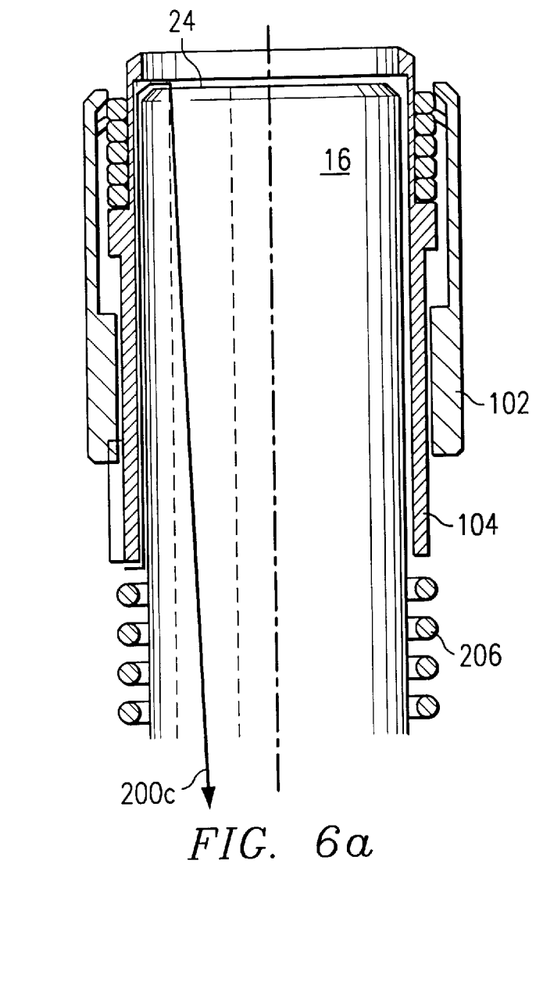
FIGS. 6a and 6b are partial, sectional views of a movable ligating band dispenser of another embodiment.
Figure 6B:
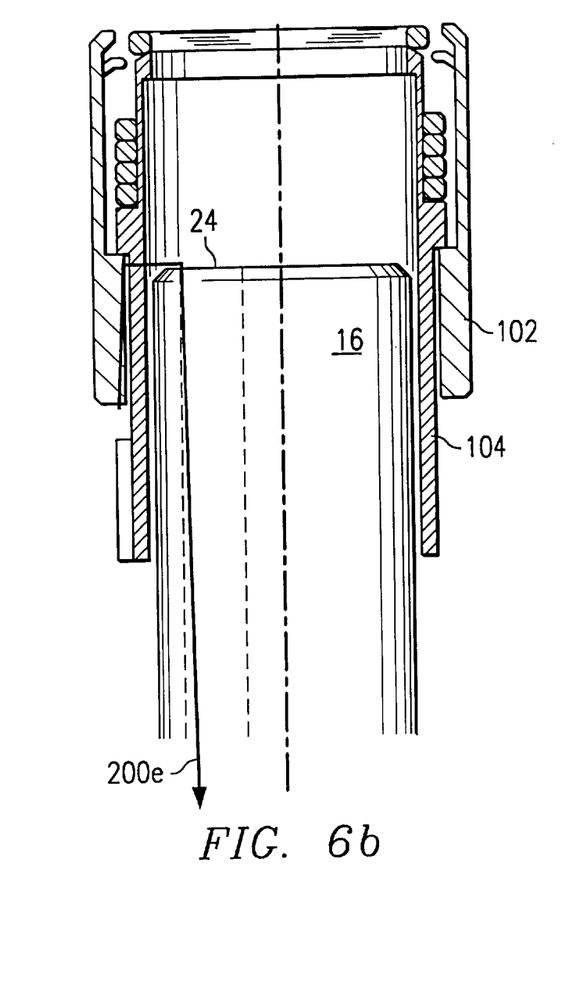

FIG. 6a preferably illustrates dispenser 100 biased proximally by spring 206. Actuating filament 200c is coupled to the proximal end of sleeve 104, and a proximally-directed force applied to filament 200c caused dispenser 100 to be extended. In contrast, FIG. 6b shows a distally-biased dispenser 100 using spring 206. Actuating filament 200c is coupled to the distal end of sleeve 104, and a proximally-directed force applied to filament 200c causes dispenser 100 to be retracted. Rather than a conventional spring, biasing element 206 may assume, for example, an elastic sleeve (not shown) or the like which functions similar to a spring and in a manner described above. For clarity, actuating filaments 200 for dispensing stored ligating bands 110 are not shown in either of these figures.

Figure 6C:
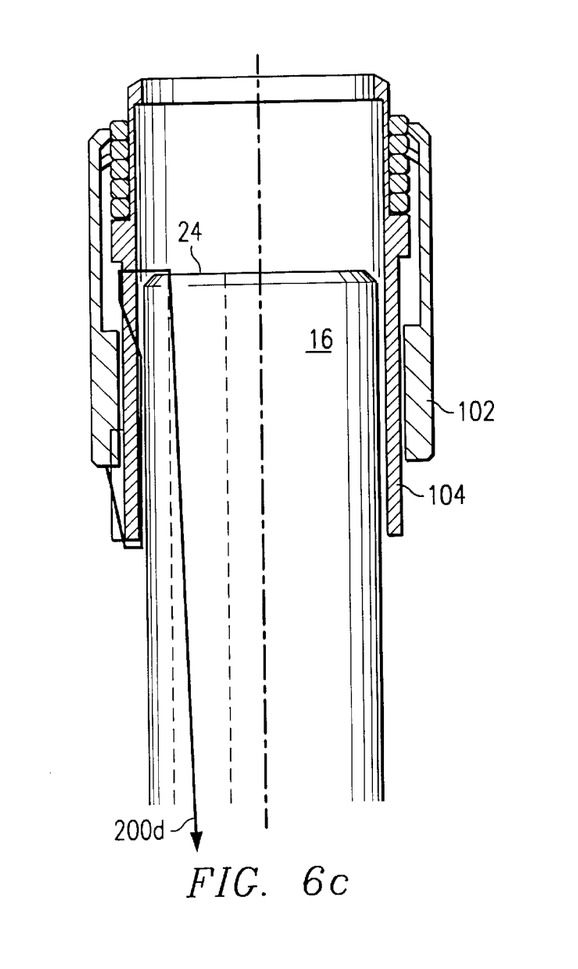
FIG. 6c is a partial, sectional view of a movable ligating band dispenser having an actuating filament.

FIG. 6c illustrates actuating filament 200d to extend sleeve 104 and retract dispensing member 102 to "load" the distal-most ligating band 110a between shoulder 114 and spring fingers 116. Actuating filament 200d is secured at a proximal end of dispensing member 102 and passes around both the proximal end of sleeve 104 and the distal end of insertion tip 16 before entering outlet 24 and the work channel of endoscope 10. Alternatively, if the configurations of either FIG. 6a or FIG. 6b are combined with the configuration illustrated in FIG. 6c, actuating filament 200d is used exclusively for readying a ligating band 110 for dispensing.

Figure 6D:
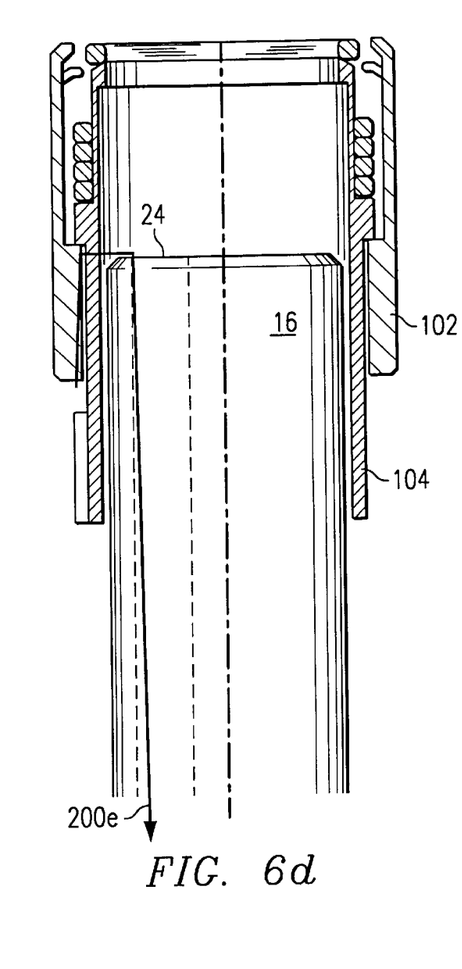
FIG. 6d is a partial, sectional view of a movable ligating band dispenser having an actuating filament.

FIG. 6d illustrates actuating filament 200e which functions to dispense a loaded ligating band 110a. Application of a proximally-directed force to actuating filament 200e causes dispensing member 102 to move distally and dispense ligating band 110a. Actuating filament 200e is secured to the proximal end of dispensing member 102 and passes around the distal end of insertion tip 16 before entering outlet 24 and the work channel extending through endoscope 10.

As actuating filaments 200d, 200e are used to load and dispense each ligating band 110, dispenser 100 of this embodiment will necessarily include both actuating filaments 200d, 200e. Accordingly, actuating filaments 200d, 200e may be independent filaments or portions of a single filament.

While the examples set forth in FIGS. 6a–6d provide specific filament attachment points and other references, one skilled in the art shall appreciate that these attachment points/references are but one set of examples, and that the actuating filaments may be joined at other points of dispenser 100 to effect the movement of dispenser 100 in a manner consistent with the present invention. Moreover, other actuating systems, for example, hydraulic or pneumatic systems (not shown) may also facilitate the extension/retraction of dispenser 100, wherein actuating elements would be fluid tubing (not shown) spanning between a pressurized fluid source and dispenser 100.

Although the above description has been directed to a specific dispenser 100, one skilled in the art shall appreciate that dispenser 100 may have a plurality of configurations, including the modification of conventional dispensers; provided, however, such configurations allow the extension and retraction of the dispenser and/or include a functioning seal that is adapted to move relative to a hosting endoscope through the movement of the dispenser.

As provided above, actuating elements 200 are coupled between dispenser 100 and controller 150. While actuating elements 200 can be manipulated directly (i.e., by hand) by the user, controller 150 enables a user to accurately and selectively control the dispensing of a stored ligating band 110 and/or the movement of dispenser 100. Controller 150 may be rather simple (for example, a filament wrapped-shaft (not shown) having filament portions 200d, 200e extending therefrom, wherein the combined tension on filaments 200d, 200e can effect the extension of dispenser 100 and rotation of the shaft while under tension effects at least the loading and dispensing of ligating band 100a); however, in reference to FIG. 7, controller 150 preferably includes user interface 152, translator 154, dispenser position controller 156, and dispenser controller 158.

Figure 7:
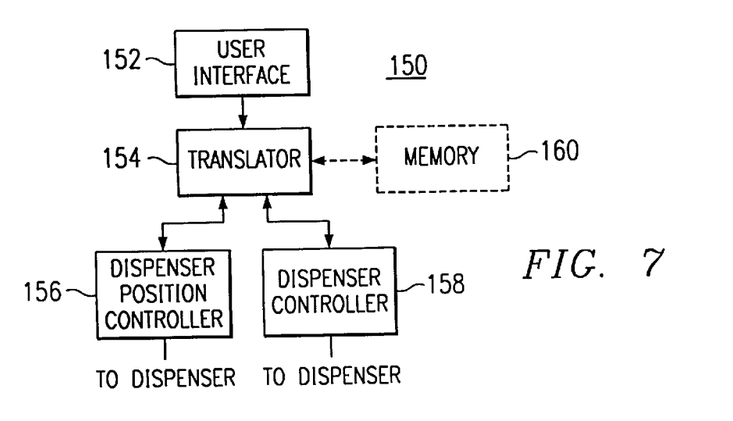
FIG. 7 illustrates one embodiment of an actuating mechanism controller in accordance with the present invention.

User interface 152 has, for example, a push button panel, a selector knob, and/or a control lever to allow a user to input desired instructions to control dispenser 100. Translator 154 receives an indication, whether electrical or mechanical, from user interface 152 and effects the user's instructions via dispenser position controller 156 and dispenser controller 158.

Translator 154 transforms input instructions to effect dispenser 100 movement and/or ligating band 110 dispersal. Depending on whether controller 150 operates mechanically or electro-mechanically, translator 154 may be a central processing unit (CPU), a linear or rotary cam, a linear or rotary shaft, or the like. If translator 154 is a CPU, controller 150 further includes memory 160, which stores programs responsive to user inputs to control the dispenser 100 movement and/or ligating band 110 dispersal. Dispenser position controller 156 and dispenser controller 158 may be pressurized fluid sources, electric motors, solenoids, cams, or the like and are responsive to translator 154 output.

While translator 154 and controllers 156, 158 generally function to move dispenser 100 and cause ligating bands 110 to be dispensed, it is desired that this system further control the actuating forces applied to perform these operations. Application of excessive force could damage dispenser 100 or cause a system malfunction. Accordingly, controller 150 translates user inputs into actuating instructions having prescribed characteristics, for example, actuating distances, applied actuating forces, and/or actuating durations, to prevent damage to dispenser 100 and to ensure systematic and consistent operation of the present invention.

Figure 8:
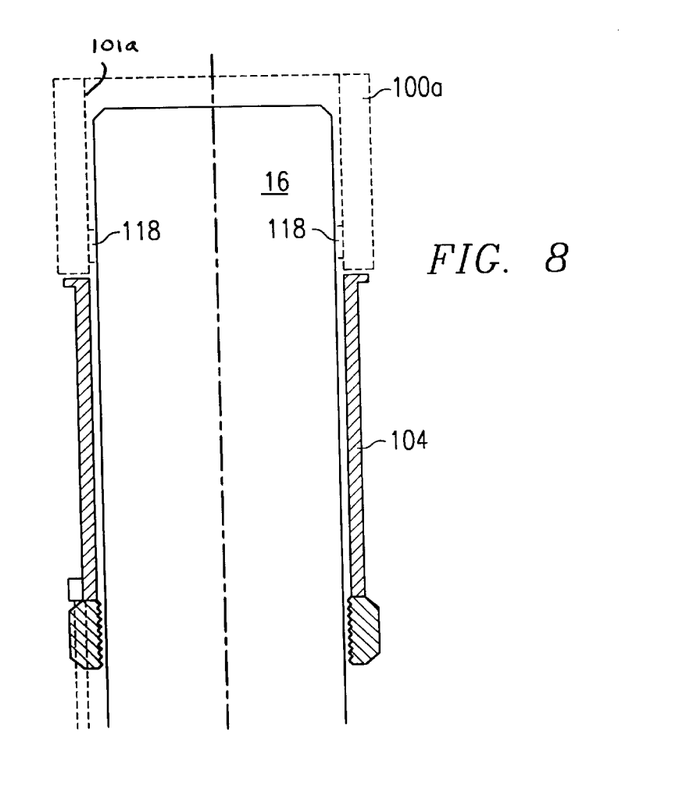
FIG. 8 is a partial, sectional view of a movable ligating band dispenser of another embodiment.

FIG. 8 illustrates another embodiment of the present invention. While platform 104 is consistent and similar to that described above, both in structure and functionality, platform 104 does not directly support one or more ligating bands 110. Rather, platform 104 includes a region, proximal to its distal end, which engages a conventional-type ligating band dispenser 110a that includes an interior dimension, which extends for at least a portion of the longitudinal length of the dispenser, that is greater than an outer dimension of the insertion tip 16 of a hosting endoscope 10. As but one example of such a dispenser, reference is hereby made to FIG. 12.

Platform 104 of this embodiment allows ligating band dispenser 100a to move from a retracted position to an extended position to improve the field of view from and mobility of an insertion tip 16 of a hosting endoscope 10. Importantly, platform 104 is operationally transparent to the dispensing operations of these ligating band dispensers. Specifically, platform 104 accommodates the respective means for dispensing ligating bands (e.g., system push rods, rotary dispensing systems, individual band filaments) of the different ligating band dispensers to enable traditional operation of these devices.

Platform 104 of this embodiment may incorporate actuating mechanisms, including controller 150 and actuating elements 200 (e.g., actuating filaments, pneumatic systems, hydraulic systems, etc.) in accordance with the examples set forth above.

As yet another alternative, a dispenser, such as that described above that and illustrated in FIG. 12, could be likewise coupled directly to an actuating mechanism, including controller 150 and actuating elements 200 (e.g., actuating filaments, pneumatic systems, hydraulic systems, etc.) in accordance with the examples set forth above.

Figure 12:
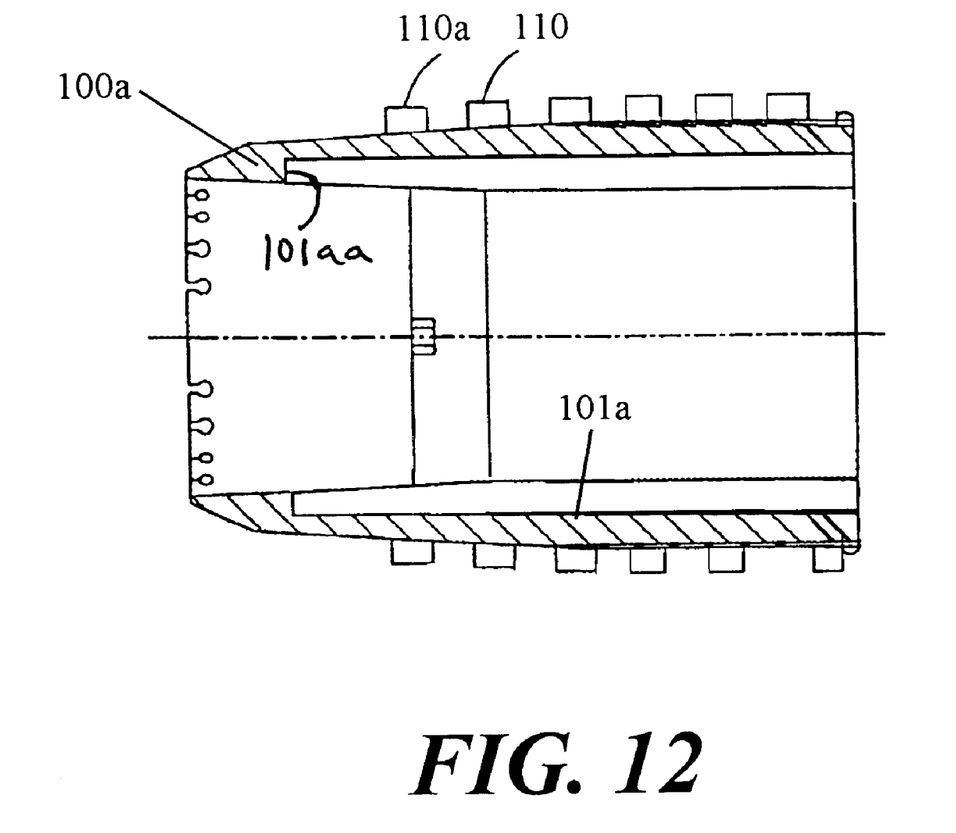
FIG. 12 illustrates an alternative embodiment of a ligating band dispenser.

Operatively, dispenser 100a is movable relative to insertion tip 16 of a hosting endoscope 10. In an extended position, much like that described above, a volume is created within an interior of dispenser 100a, and in a retracted position, such volume would be significantly reduced so as to provide a greater field of view for the optical portion of the hosting endoscope. In the retracted position, the face of insertion tip 16 would abut stop surface 10aa of dispenser 100a. Stop surface 10aa ensures that dispenser 100a is retracted to a specific position.

Providing an example of the operation of the present invention, reference will be made to a dispenser 100 having features illustrated in FIGS. 6a, 6c, and 6d, including proximally-biased spring 206 and actuating filaments 200d, 200e.

Dispenser 100 is positioned on the insertion tip 16 of a hosting endoscope 10. Actuating filaments 200 are passed through the work channel of the hosting endoscope 10 and through inlet 28 to the endoscope control portion 12. Actuating filaments 200 are coupled to, for example, controller 150.

For the purpose of this example, dispenser 100 begins in a retracted position. Insertion tip 16 is inserted into a patient, for example, through the mouth, to observe certain internal regions. Dispenser 100 remains in a retracted position during travel of the insertion tip 16 so as to provide the user the broadest field of view detectable by the endoscope image sensing device. Once tissue has been targeted for ligation, the user requests extension of dispenser 100. Controller 150 applies a proximally-directed force to actuating filament 200d for a predetermined time causing dispenser 100 to be extended, thus creating volume 112 defined by the interior surface of sleeve 104. After extension, opening 111 is positioned adjacent to the targeted tissue. The user applies a suction to the appropriate insertion tip 16 outlet, drawing the targeted tissue into volume 112.

The user then requests dispersal of a single ligating band 110a. If ligating band 110a was not loaded by the previous control of actuating filament 200d, controller 150 applies a proximally-directed force to actuating filament 200d for a predetermined duration causing ligating band 100a to be selected. Controller 150 then releases actuating filament 200d to apply a proximally-directed force to actuating filament 200e for a predetermined duration, thus causing ligating band 100a to be dispensed. Upon dispensing a ligating band from dispenser 100, the dispensed ligating band attempts to assume its non-expanded dimensions. As the subject tissue is positioned within an inner diameter of the ligating band, constriction of the band effectively ligates the subject tissue. The applied suction is ceased, and the insertion tip 16 moved away from the ligated tissue. If further exploration is required, actuating filaments 200d, 200e are released and spring 206 biases dispenser 100 again to a retracted position.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A ligating device adapted to be movably received on an insertion portion of the distal end of an endoscope, the ligating device comprising:
   a seal adapted to be affixed to the distal end of the endoscope; and
   a dispensing device for supporting at least one ligating band and having a proximal end adapted to receive the insertion portion of the endoscope, a distal end, and an interior surface;
   wherein, when in an operative position with respect to the endoscope, the interior surface at least partially encompasses a portion of the insertion portion of the endoscope and at least a portion of the seal,
   wherein the dispensing device is capable of movement from a retracted position to at least a dispensing position, where for the dispensing position the distal end of the dispensing device is spaced from the distal end of the endoscope, creating a volume substantially defined by the dispensing device, sufficient to perform a ligation procedure, and in the retracted position the volume is reduced relative to the volume at the dispensing position, and
   wherein the seal is adapted to establish a sealing relationship between the endoscope and the dispensing device during a ligation procedure.

2. A ligating device according to claim 1, further comprising an actuating mechanism, coupled to the dispensing device, to selectively effect movement of the dispensing device from at least the dispensing position to the retracted position.

3. A ligating device according to claim 1, wherein at least a portion of an exterior surface of the dispensing device is adapted to support a plurality of ligating bands.

4. A ligating device according to claim 1, wherein the seal includes a tubular portion that encompasses a portion of the insertion portion of the endoscope, and the proximal end of the dispensing device moveably receives at least that portion of the insertion portion of the endoscope encompassed by the seal.

5. A ligating device according to claim 1, wherein the proximal end of the dispensing device includes a deformable member, and the dispensing device when in the operative position, is adapted to engage the seal through at least the deformable member.

6. A ligating device according to claim 1, wherein the seal is adapted to frictionally contact the interior surface of the dispensing device.

7. A ligating device comprising:
   a sealing structure adapted to be affixed to the distal end of an insertion portion of an endoscope; and
   a dispensing device for supporting at least one ligating band and having a proximal end adapted to be movably received on the distal end of the insertion portion of the endoscope, a distal end, and an interior surface adapted to sealingly engage the sealing structure;
   wherein, when the dispensing device is operatively positioned relative to the insertion portion of the endoscope, a seal is established between the dispensing device and the endoscope, and
   wherein the dispensing device is capable of movement from a retracted position to at least a dispensing position, where for the dispensing position the distal end of the dispensing device is spaced from the distal end of the endoscope, creating a volume substantially defined by the dispensing device, sufficient to perform a ligation procedure, and in the retracted position the volume is reduced relative to the volume at the dispensing position.

8. A ligating device according to claim 7, further comprising an actuating mechanism, coupled to the dispensing device, to selectively effect movement of the dispensing device from at least the dispensing position to the retracted position.

9. A ligating device according to claim 7, wherein at least a portion of an exterior surface of the dispensing device is adapted to support a plurality of ligating bands.

10. A ligating device according to claim 7, wherein the interior surface includes an inwardly projecting abutting surface.

11. A ligating device according to claim 10, wherein a distance between the proximal end of the dispensing device and the abutting surface is substantially equal to a range of motion between the dispensing position and the retracted position.

12. A ligating device according to claim 7, wherein the sealing structure includes a tubular portion that, when affixed to the endoscope, is adapted to extend about the distal end of the insertion portion, and the proximal end of the dispensing device, when operatively positioned relative to the endoscope, is adapted to moveably receive that portion of the insertion portion that is encompassed by the sealing structure.

13. A ligating device according to claim 12, wherein the proximal end of the dispensing device includes a deformable member, and the dispensing device, when operatively positioned relative to the endoscope, is adapted to engage the sealing structure through at least the deformable member.

14. A ligating device according to claim 7, wherein the sealing structure is adapted to operatively maintain a frictional contact with the interior surface of the dispensing device.

15. A ligating band dispensing device comprising:

a ligating band dispenser, adapted to be slidably mounted on a distal end of an insertion portion of an endoscope, having a proximal end and a distal end;

a sealing member adapted to be fixed proximate to the distal end of the insertion portion of the endoscope to establish a seal between an interior surface of the dispenser and the endoscope; and an actuating mechanism, coupled to the ligating band dispenser, and when the dispenser is mounted on the endoscope, to selectively effect movement of the dispenser from a first position to at least a second position, relative to the sealing member when fixed to the insertion portion of the endoscope, wherein in the second position, the distal end of the dispenser is distally spaced from the distal end of the endoscope, creating a volume substantially defined by the dispenser sufficient to perform a ligation procedure, and in the first position the volume is reduced to expose, at least in part, a face of the distal end of the insertion portion of the endoscope.

16. A ligating band dispensing device according to claim 15, wherein at least a portion of all exterior surface of the dispenser is adapted to support a plurality of ligating bands.

17. A ligating band dispensing device according to claim 15, wherein the sealing member includes a cylindrical portion, that, when fixed to the endoscope encompasses a portion of the distal end of the insertion portion of the endoscope.

18. A ligating band dispensing device according to claim 17, wherein the proximal end of the dispenser includes a deformable member, and the dispenser, when mounted on the endoscope, engages the sealing member through at least the deformable member.

19. A ligating band dispensing device according to claim 15, wherein the sealing member is adapted to operatively maintain a frictional contact with an interior surface of the dispensing device.

20. A system for dispensing a ligating band to ligate tissue, the system comprising:

an endoscope having an insertion portion for insertion into a patient;

a member, positioned on the insertion portion of the endoscope, having a proximal end that includes an abutting surface to abut a distal face of the insertion portion of the endoscope; and a dispensing device, movably positioned on the insertion portion of the endoscope, capable of movement from a retracted position to at least a dispensing position, where for the dispensing position a distal end of the dispensing device is spaced from the distal face of the insertion portion of the endoscope, creating a volume substantially defined by the dispensing device, sufficient to perform a ligation procedure, and in the retracted position the volume is substantially diminished, wherein at least a portion of the member is interposed between the dispensing device and the endoscope.

21. A system in accordance with claim 20, further comprising an actuating mechanism, coupled to the dispensing device, to selectively effect movement of the dispensing device from at least the dispensing position to the retracted position.

22. A system in accordance with claim 20, wherein at least a portion of an exterior surface of the dispensing device is adapted to support at least one ligating band.

23. A system in accordance with claim 20, wherein the abutting surface includes a sealing member to effect a seal between an interior surface of the dispensing member and the endoscope.

24. A system for dispensing a ligating band to ligate tissue, the system comprising:

an endoscope having an insertion portion for insertion into a patient;

a member, positioned on the insertion portion of the endoscope, having a proximal end that includes an abutting surface to abut a face of the insertion portion of the endoscope; and a dispensing device, movably positioned on the insertion portion of the endoscope, capable of movement from a retracted position to at least a dispensing position, where for the dispensing position a distal end of the dispensing device is spaced from the face of the insertion portion of the endoscope, creating a volume substantially defined by the dispensing device, sufficient to perform a ligation procedure, and in the retracted position the volume is reduced relative to the volume at the dispensing position, wherein at least a portion of the member is interposed between the dispensing device and the endoscope, and wherein the member operatively establishes a seal between the endoscope and the dispensing device throughout any movement of the dispensing device.

* * * * *